US 6,582,467 B1

(12) United States Patent
Teitelbaum et al.

(10) Patent No.: US 6,582,467 B1
(45) Date of Patent: Jun. 24, 2003

(54) EXPANDABLE FUSION CAGE

(75) Inventors: George Teitelbaum, Santa Monica, CA (US); Samuel M. Shaolian, Newport Beach, CA (US); To V. Pham, Trabuco Canyon, CA (US); Thanh V. Nguyen, Irvine, CA (US)

(73) Assignee: Vertelink Corporation, Irvine, CA (US)

( * ) Notice: Subject to any disclaimer, the term of this patent is extended or adjusted under 35 U.S.C. 154(b) by 0 days.

(21) Appl. No.: 10/003,727

(22) Filed: Oct. 31, 2001

Related U.S. Application Data
(60) Provisional application No. 60/245,104, filed on Oct. 31, 2000.

(51) Int. Cl.$^7$ ................................................ A61F 2/44
(52) U.S. Cl. ........................ 623/17.11; 623/17.11; 623/17.12
(58) Field of Search ................ 623/17.11, 17.12, 623/17.13, 17.15, 17.16; 606/61

(56) References Cited

U.S. PATENT DOCUMENTS

| 4,733,665 | A | * | 3/1988 | Palmaz | |
| 4,904,260 | A | * | 2/1990 | Ray et al. | 623/17 |
| 5,015,247 | A | * | 5/1991 | Michelson | 606/61 |
| 5,059,193 | A | * | 10/1991 | Kuslish | 606/61 |
| 5,571,189 | A | * | 11/1996 | Kuslich | 623/17 |
| 5,674,295 | A | * | 10/1997 | Ray et al. | 623/17 |
| 5,989,290 | A | * | 11/1999 | Biedermann et al. | 623/17 |
| 6,015,436 | A | * | 1/2000 | Schonhoffer | 623/17 |
| 6,022,376 | A | * | 2/2000 | Assell et al. | 623/17 |
| 6,129,763 | A | * | 10/2000 | Chauvin et al. | 623/17 |
| 6,149,651 | A | * | 11/2000 | Drewry et al. | 606/61 |
| 6,174,334 | B1 | * | 1/2001 | Suddaby | 623/17.11 |
| 6,176,882 | B1 | * | 1/2001 | Biedermann et al. | 623/17.15 |

* cited by examiner

Primary Examiner—Ralph A. Lewis
(74) Attorney, Agent, or Firm—Knobbe Martens Olson & Bear LLP

(57) ABSTRACT

Disclosed is an expandable fusion cage which facilitates the fusion of adjacent bony surfaces, preferably those in the spine. In a preferred embodiment, the fusion cage. The surfaces of the cage which are intended to contact the vertebral endplates have multiple portions cut out of the metal to form sharp barbs. As the cage is expanded to come into apposition with endplates above and below, the sharp barbs protrude into the subcortical bone of the vertebral body thus securing the cage in place. Multiple holes or fenestrations are present on the superior and inferior surfaces of the cage to permit contact of morselized autologous bone and/or an artificial bone matrix material with the prepared endplate surface.

7 Claims, 2 Drawing Sheets

EXPANDABLE FUSION CAGE

RELATED APPLICATION DATA

This application claims priority under 35 U.S.C. §119(e) to Provisional Application Ser. No. 60/245,104, filed Oct. 31, 2000.

BACKGROUND OF THE INVENTION

1. Field of the Invention

This invention relates to bone fusion devices, more specifically, it relates to devices which aid in the fusion of adjacent vertebral bodies in the spine.

2. Description of the Related Art

Fusion cages provide a space for inserting a bone graft between adjacent portions of bone. In time, the bone and bone graft grow together through or around the fusion cage to fuse the graft and the bone solidly together. Fusion cages may be used to connect any adjacent portions of bone, however one use is in the spine. Spinal fusion cages are primarily used in the lumbar spine, although they may also be used in the cervical or thoracic spine as well. Fusion cages can be inserted in the lumbar spine using an anterior, posterior, or lateral approach.

Spinal fusion cages are cylindrical, threaded, hollow metallic orthopedic implants with multiple side holes. Known fusion cages are constructed from a variety of materials including titanium alloys, porous tantalum, other metals, allograft bone, or ceramic material. These implants are generally designed to be filled with autologous bone material and then threaded into the disc space between two adjacent vertebral bodies. There they help to promote bony fusion between the two adjacent vertebral levels that prevents relative motion between the two vertebral levels affected by spinal instability due to generative changes and/or previous laminectomy, and other conditions associated with pain with vertebral motion.

Fusion cages are generally inserted by first opening the disc space between two vertebrae of the lumbar spine using a wedge or other device on a first side of the vertebrae. Next, a tapered plug is hammered in to hold the disc space open. A threaded opening is then drilled and tapped on a second side opposite the first side of the vertebrae for producing the equivalent of a "split" threaded bore defined by the walls of the vertebrae above and below the bore. The threaded fusion cage is then threaded into the bore and the wedge is removed. The first side is then drilled and tapped before inserting a second threaded fusion cage. Typically, two threaded fusion cages are used at each invertebral disc level.

SUMMARY OF THE INVENTION

In accordance with a preferred embodiment, there is provided an expandable fusion cage. The cage comprises a tubular body having first and second open ends and a wall surface disposed between the first and second ends, in which the wall surface is formed by a plurality of intersecting elongate members, at least some of which intersect with one another at one or more points intermediate the first and second ends of the tubular body. The wall surface has a superior portion and an inferior portion, wherein the superior and inferior portions are opposite each other and each have an outer surface with a plurality of barbs thereon which extend away from the tubular body. The wall surface further defines a space inside the body that is filled with a natural and/or artificial material to stimulate bone growth. The tubular body has a first diameter which permits delivery of the tubular body into a space formed between two vertebral bodies and a second, expanded diameter, wherein expansion of the tubular body expands the space between the two vertebral bodies. In a preferred embodiment, the fusion cage further comprises a capsule surrounding the material to stimulate bone growth, wherein the portions of the capsule directly adjacent to the tubular body comprise a relatively impermeable thin layer of material and the portions of the capsule adjacent to the first and second open ends comprise a material permeable by the material to stimulate bone growth.

DETAILED DESCRIPTION OF THE PREFERRED EMBODIMENT

Figure 1A:
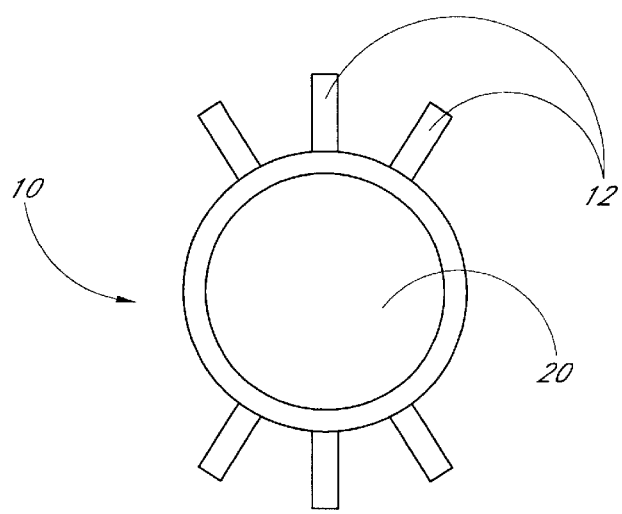
FIG. 1A is a cross-section of a preferred embodiment of a fusion cage.
Figure 1B:
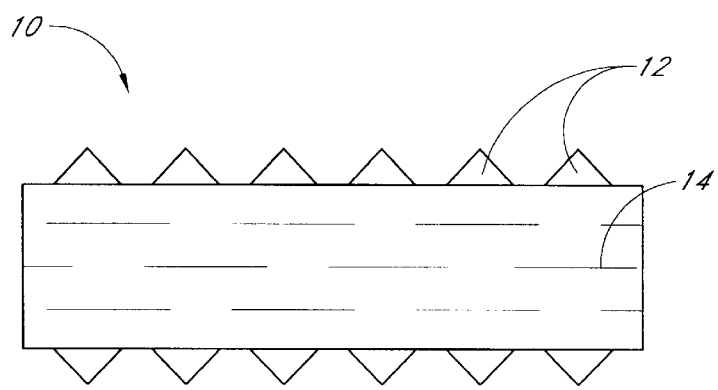
FIG. 1B is a plan view of a preferred embodiment of an unexpanded fusion cage in which the struts are fixedly secured at each intersection.
Figure 1C:
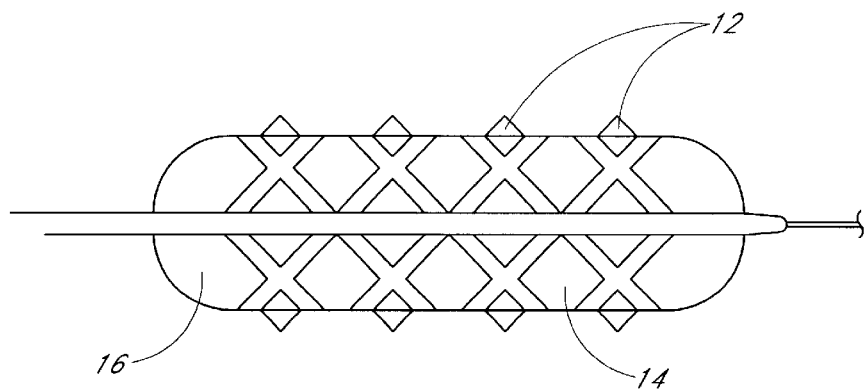
FIG. 1C is a plan view of a preferred embodiment of a fusion cage as in FIG. 1B which is expanded on a balloon.
Figure 2:
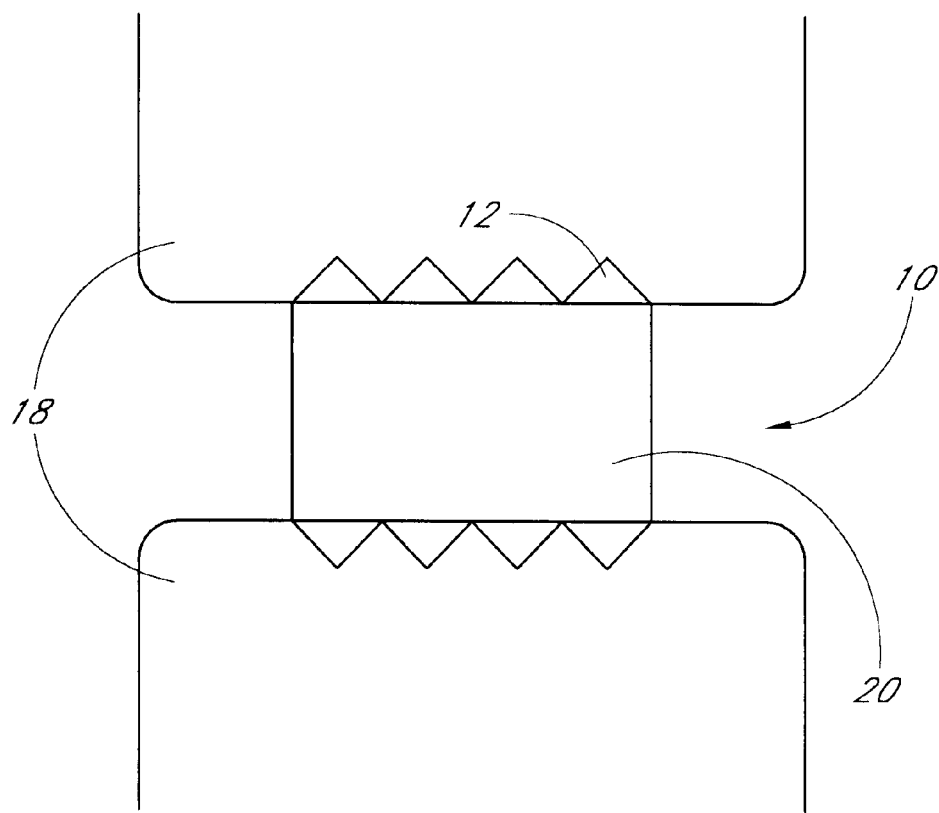
FIG. 2 is a cross section through two adjacent vertebral bodies having a fusion cage implanted therebetween.

Disadvantages associated with spinal fusion cages include a large surgical incision necessary for the exposure of the intervertebral space and actual insertion of the cage. Either a posterior or anterior surgical approach is used for their implantation. This invasive open surgery can be fraught with complications including hemorrhage, infection, bowel damage, ileus, and nerve damage. In addition, non-union, or failure of bony fusion (leading to a painful pseudarthrosis) may occur following cage implantation. The cylindrical shape of cages and the thickness of their metallic walls both act to limit the contact surface area of cages with the adjacent vertebral body endplates, between which cages are intended to promote bony fusion.

Herein is described several versions of a novel device intended to overcome some of the disadvantages of known spinal fusion cages. In one embodiment there is an expandable cage 10 that is generally round or ovoid in cross section. The surfaces intended to contact the vertebral endplates have multiple portions cut out of the metal to form sharp barbs 12. As the cage is expanded to come into apposition with endplates above and below, the sharp barbs 12 protrude into the subcortical bone of the vertebral body 18 thus securing the cage in place. The cage is preferably designed to expand so as to permit the superior and inferior surfaces to flatten against the endplate thereby increasing the surface area of contact of the cage with the endplate. Multiple holes or fenestrations are present on the superior and inferior surfaces of the cage to permit contact of morselized autologous bone and/or an artificial bone matrix material with the prepared endplate surface. In one embodiment, Healos (Orquest, Inc.) combined with bone marrow and/or an orthobiological agent to promote bone growth is within the case. In preferred embodiments, the morselized autologous bone and/or an artificial bone matrix 20 contained in the cage is in the form of a paste-like slurry.

The endplate surface can be prepared by percutaneous means using a transcatheter angled drilling device to abrade the cortical surface of the endplate. The thin metallic wall of the expandable cage, which is thinner than conventional surgical fusion cages, further enhances the chances of contact of morselized bone and/or artificial bone matrix within the cage with the bony endplates. The aforementioned morselized bone and/or artificial bone matrix material with bone marrow and possibly orthobiological agents is preferably introduced into the expandable fusion cage through a catheter after the implantation of the cage using the same posterolateral paraspinous pathway used for the implantation of the cage. There may also be a thin compliant silicone rubber or other suitable expansile plastic layer incorporated into the walls of the cage, but not in contact with the endplates, intended to prevent seepage of the injected material through the openings 14 between the struts of the expanded cage into the disc space. Leakage of the injected material from the open ends of the expanded cage could be accomplished by the placement of a plug of a generally porous material including, but not limited to, a resorbable collagen material, such as Avitene sponge, or an expansible membrane of silicone rubber or C-flex covering the ends of the cage.

The cages may be either completely balloon expandable or may be partially self-expanding but requiring additional balloon expansion to seat sharp stabilization barbs within the bony endplates. A generally ovoid cross sectional configuration of this embodiment of the cage can be conferred upon the device by expansion using twin high-pressure balloons aligned in a parallel, over-under arrangement. The balloons are inflated simultaneously and are fixed in the appropriate over-under orientation by incorporation of their inflation lumen into a semi-rigid plastic or metallic band. A preferred orientation of the band is that having its edges facing or perpendicular to the vertebral endplates. The structure of a preferred semi-rigid band permits its flexion only posteriorly and around the long axis of the vertebral column. The band is preferably incapable of twisting on itself. Consequently, the inflation balloons together with the expandable cage, which is crimped onto the balloons in a unexpanded state for delivery into the disc space, are maintained in an appropriate orientation to implant the cage with its fixation barbs directed toward the endplate surfaces.

The cage, once expanded and filled with materials described above, may be used not only to promote bony union between the neighboring vertebral levels but also to raise the height of the intervertebral disc space, especially in cases of fusion performed for severe degenerative disc disease. To this end, in a preferred embodiment, the expanded cage possesses sufficient hoop strength to prevent its collapse under physiologic spinal axial loads with the patient in an erect position. This may be assisted by hardening of an artificial bone matrix material used to fill the cage after its deployment, possibly utilizing a preparation of hydroxyapatite.

The deployment of the expandable cage is a multi-step process. One preferred method proceeds as follows. With the patient in the prone position and under fluoroscopic guidance, an approximately 12 French stiff plastic or metallic delivery sheath is percutaneously advanced into the intervertebral disc space of the neighboring vertebral bodies to be fused via a posterolateral, paraspinous approach. The spinal nerve root in the vicinity of the paraspinous approach may be avoided by initially entering the target disc space with a "skinny" needle capable of detecting electrical impulses while simultaneously delivering low-grade electrical stimulation to the expected dermatome distribution of the spinal nerve root at risk. With the detection of increased impulses through the skinny needle, the needle is withdrawn and slightly redirected. In a preferred embodiment, a second, contralateral sheath having a lower profile is placed into the disc space that allows capture of a guidewire inserted via the larger sheath. This permits more effective "through-and-through" access (control of both ends of a guidewire) into the disc space.

Next, the disc space is prepared to accept the cage implant. This is preferably accomplished by creating a disc cavity by the removal of nuclear material (nucleus pulposus) using a previously described expandable rotating blade system connected to a drive shaft surrounded by an "Archimedes screw" structure. The concurrent action of the rotating blade assembly, Archimedes screw, and applied suction will remove disc material through the delivery sheath. The adjacent upper and lower vertebral endplates are then abraded with an angled bone drill device. This is followed by expansion of the height of the disc space using a high-pressure, preferably non-compliant, dilation balloon catheter placed within the disc cavity.

The delivery sheath is then advanced into the carved-out, expanded disc cavity, and then the cage, mounted on the dual-balloon expansion system, is advanced through the sheath to the deployment site. The semi-rigid band structure aids to push the balloons and the mounted cage through the sheath, all the while maintaining the proper deployment orientation of the cage.

The cage is then expanded thus preserving the newly increased disc space height. The cage is subsequently filled with an artificial bone matrix material with additives or morselized autologous bone with or without matrix material, such as is mentioned above. The delivery sheath is then removed and the procedure is completed.

One variation in design includes the attachment of a small wire that is left extending from the disc space, back through the delivery sheath tract, and finally connected to a small battery-powered electrical current generator buried under the skin near the insertion site. By delivering a low-trade electrical current to the metallic cage, through the wire, bone growth can be stimulated.

A single cage may be deployed centrally within the disc space. Alternatively, bilateral cages may be deployed within the disc space.

In an alternate embodiment, the expandable spinal fusion cage is a balloon expandable metallic cage that is inserted along the vertical axis of the spinal column from one adjoining vertebral body to the next across the intervening disc space. The expanded diameter of the cage is preferably about 8–10 mm. The length of the cage is preferably about 3 cm. The cage preferably incorporates a thin, compliant, expandable plastic or silicone rubber sleeve that aids in the prevention of leakage of any material contained in the cage (e.g., bone matrix material injected into the cage) through the struts of the expanded cage into the disc space through which the cage passes.

The cage preferably has features similar to those found in endovascular and biliary balloon-expandable stents, such as the Palmaz stent (Johnson & Johnson). The cage is composed of stainless steel or other expandable metal alloy having great tensile strength. One design possibility is a small tube composed of collapsed metal struts linked to one another by laser or spot welding or the design of the collapsed struts could be carved into a hollow metal tube using any of a variety of means, including laser energy. Numerous strut designs are possible that would allow balloon expansion of the cage.

Alternatively, the cages used can be self-expanding, including those which are made up of flexible interwoven metal wires or multiple small metal rings each welded to adjacent rings. Preferably each ring in such a design has a zigzag configuration. Both the interwoven wire and multiple zigzag ring designs can be highly compressed so as to fit within a delivery sheath. Once advanced to the delivery site, the cage is unsheathed and allowed to expand to similar dimensions mentioned above for the balloon-expanded vertical fusion cage. The self-expanding cages can likewise incorporate an expandable thin sleeve that prohibits or minimizes side leakage through the cage struts.

The vertical cage creates a "pillar" of artificial bone matrix material (preferably with the aforementioned additives) between two neighboring vertebral bodies to effect bony fusion between the two bodies. The vertical cage is inserted using a multi-step process, a preferred embodiment of which proceeds as follows.

First, under fluoroscopic guidance and with the patient in the prone position, a bone pin is percutaneously hammered into the posterolateral aspect of the upper vertebral body to be fused. Next, a metallic sheath with a beveled end is hammered into the same vertebral body over the bone pin. The bone pin is removed and the bevel of the metallic sheath is turned inferiorly.

Through the beveled metallic sheath, a right (90°) angled about 11–13 gauge nitinol needle with central stylet (similar to the Osteo RX needle made by Cook) is inserted into the beveled entry sheath with the nitinol needle having been chilled. The bevel of the metallic guiding sheath directs the emerging nitinol needle inferiorly as it is hammered into the vertebral body, through the subjacent intervertebral disc and into the caudaladjoining vertebral body. The stylet is removed and a large-bore stiff guidewire is advanced through the nitinol needle into the lower vertebral body. Through the guiding sheath, an over-the-wire high-speed ovoid drill bit connected to a flexible drive shaft with an associated Archimedes screw structure is inserted with its own catheter over the heavy-duty guidewire. This device serves to drill out a channel, preferably about 4 mm wide, through the adjoining vertebral bodies.

A second drilling device, described elsewhere, possessing a distal metal capsule and side window or trough as well as a high-pressure sturdy balloon situated on the surface of the capsule opposite the trough, is then advanced through the about 4 mm channel into the vertical bone tract extending between the neighboring vertebral bodies. The above device possesses a rotating ovoid drill bit connected to a drive shaft that is moved to and fro within the trough while gradually inflating the side balloon in order to push the drill bit into the bony sidewall. This process is performed under fluoroscopic guidance, with the capsule rotated through all quadrants of all segments of this vertical bone channel until a channel diameter of about 8–10 mm is achieved.

The specialized drilling device is then exchanged over the heavy-duty guidewire for the cage delivery sheath/catheter. The cage, depending upon the design used, is either balloon expanded or self-expanded at the appropriate site bridging the intervertebral disc space with the open ends of the cage located within the upper and lower vertebral bodies.

The dead space within the expanded vertical cage is then filled with either morselized autologous bone or without bone matrix agent, or an artificial bone matrix material combined with bone marrow and/or an orthobiological agent.

The entry sheath is then removed from the cephalad vertebral body and the procedure is completed.

Like the horizontally oriented intradiscal cage, insertion of the vertical transdical cage may be preceded by balloon inflation within the disc space in order to heighten the disc space. Also, the vertical cage may incorporate a low-grade electrical current supplied by an implanted battery-powered energy source in an effort to stimulate bone growth. Both types of percutaneously inserted fusion cages could also be used with posterior fusion effected by the use of a percutaneously implanted pedicle screw and inflatable rod system as described in U.S. patent application No. 09/747,066, filed Dec. 21, 2000 which is hereby incorporated by reference in its entirety.

There are several other potential designs for percutaneously inserted spinal fusion cages. One is an intradiscal circular band made up of multiple columns of nitinol wire zigzags, in which the to and for axis of the wire zigzags is oriented parallel to the vertebral endplates. The entire wire zigzag structure is preferably constructed from a single length of wire, and is also self-expanding. For purpose of introduction, it is compressed down and placed within a delivery capsule. The correct cage orientation for appropriate deployment is maintained by the same semi-rigid band design described above. The delivery capsule is advanced through an introduction sheath into the central portion of the disc space which has been prepared to receive this cage by prior extraction of disc material using methods described above. Once unsheathed from its capsule, the cage expands radially and axially. A thin layer of compliant biocompatible rubber or plastic material is preferably incorporated into the design of this self-expanding cage to prevent or minimize leakage into the surrounding disc space of any bone fusion-enhancing material introduced into the center of the cage following deployment. Alternatively, a compliant, detachable balloon with numerous microscopic holes or fenestrations may be inserted into the central dead space of the cage following deployment of the cage and loaded on a catheter extending through a self-sealing valve on the balloon. The balloon is then filled or inflated with artificial bone matrix material combined with marrow and/or an orthobiological agent until the balloon expands to abut the endplate surfaces. The catheter is then detached from the balloon by applied traction while the self-sealing valve prevents loss of the paste-like slurry from the balloon's lumen. The microscopic holes in the balloon allow for in growth of blood vessels and osteoblastic cells from the adjacent endplates which had been prepared immediately prior to cage deployment by drill abrasion. This concept of depositing bone fusion-enhancing material within a detachable balloon could be utilized with all the other cage designs mentioned herein above.

In another embodiment, an intradiscal horizontal circular band composed of a single length of nitinol wire is fashioned into many tightly spaced vertically oriented zigzags. Insertion of this device includes cooling the device below freezing and stretching it out horizontally until it can be advanced through the delivery sheath without impediment. Once implanted, it will warm and regain its previous structure.

In another embodiment, a coil-shaped heavy-gauge nitinol wire that is introduced at cold temperatures through an about 8–11 gauge needle into the disc space. Once the nitinol wire becomes exposed to body temperature just beyond the tip of the insertion trocar, it begins to reassume its intended shape. As described above, the disc space is first prepared to receive the coil implant. Once deployed, bone fusion-enhancing material could be retained within the coil using the aforementioned detachable balloon having microfenestrations. In a preferred embodiment, the coil is designed so as to have an angled needle segment at the leading end of the coil that can be hammered into an adjacent vertebral body to stabilize the emerging coil.

A preferred bone drilling device is described in applicant's co-pending application entitled "Bone Drilling Device", 10/004,279, filed Oct. 31, 2001, which is hereby incorporated by reference in its entirety, Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. An expandable fusion cage, comprising:

a tubular body having first and second open ends and a wall surface disposed between the first and second ends, the wall surface being formed by a plurality of intersecting elongate members, at least some of the elongate members intersecting with one another intermediate the first and second ends of the tubular body and said wall surface defining a space inside the body;

the wall surface having a superior portion and an inferior portion, wherein the superior and inferior portions are opposite each other, the superior and inferior portions each having an outer surface having a plurality of barbs thereon extending away from the tubular body; and the space inside the body being filled with a natural and/or artificial material to stimulate bone growth;

wherein the tubular body has a first diameter which permits delivery of the tubular body into a space formed between two vertebral bodies and a second, expanded diameter, wherein expansion of the tubular body expands the space between the two vertebral bodies.

2. An expandable fusion cage according to claim 1, wherein the plurality of elongate members are a plurality of wires.

3. An expandable fusion cage according to claim 2, wherein the wires are fixedly secured to one another where the wires intersect with one another.

4. An expandable fusion cage according to claim 1, wherein the plurality of elongate members are a plurality of thin bars which are fixedly secured to one another where the bars intersect with one another.

5. An expandable fusion cage according to claim 1, further comprising a capsule surrounding the material to stimulate bone growth, wherein the portions of the capsule directly adjacent to the tubular body comprise a relatively impermeable thin layer of material and the portions of the capsule adjacent to the first and second open ends comprise a material permeable by the material to stimulate bone growth.

6. An expandable fusion cage according to claim 1, wherein the cage is self-expanding.

7. An expandable fusion cage according to claim 1, wherein the cage is expanded with the aid of a balloon.

* * * * *